US012672899B2

(12) United States Patent
Biedermann et al.

(10) Patent No.: US 12,672,899 B2
(45) Date of Patent: Jul. 7, 2026

(54) RECEIVING PART OF A BONE ANCHORING DEVICE AND SYSTEM INCLUDING THE RECEIVING PART AND AT LEAST ONE INSTRUMENT

(71) Applicant: BIEDERMANN TECHNOLOGIES GMBH & CO. KG, Donaueschingen (DE)

(72) Inventors: Timo Biedermann, Trossingen (DE); Lutz Biedermann, VS-Villingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/272,751

(22) Filed: Jul. 17, 2025

(65) Prior Publication Data

US 2026/0033867 A1 Feb. 5, 2026

Related U.S. Application Data

(60) Provisional application No. 63/678,208, filed on Aug. 1, 2024.

(30) Foreign Application Priority Data

Aug. 1, 2024 (EP) ..................................... 24192465

(51) Int. Cl.
*A61B 17/70* (2006.01)
*A61B 17/00* (2006.01)

(52) U.S. Cl.
CPC ...... *A61B 17/7032* (2013.01); *A61B 17/7074* (2013.01); *A61B 2017/00477* (2013.01)

(58) Field of Classification Search
CPC ............ A61B 17/7032; A61B 17/7035; A61B 17/7037; A61B 17/7038
See application file for complete search history.

(56) References Cited

U.S. PATENT DOCUMENTS

| 9,393,049 | B2* | 7/2016 | Jones | .................. A61B 17/7086 |
| 10,299,839 | B2* | 5/2019 | Sicvol | ................ A61B 17/7076 |

(Continued)

FOREIGN PATENT DOCUMENTS

| EP | 2 713 913 B1 | 10/2018 |
| EP | 3 878 386 A1 | 9/2021 |

(Continued)

OTHER PUBLICATIONS

Extended European Search Report for Application No. 24192465.3, dated Jan. 24, 2025, 9 pages.

*Primary Examiner* — Jacqueline T Johanas
(74) *Attorney, Agent, or Firm* — Womble Bond Dickinson (US) LLP

(57) ABSTRACT

A receiving part of a bone anchoring device has a first end, a second end, and a central axis, a rod recess adjacent to the first end for receiving a rod, the rod recess forming two legs, a groove that extends circumferentially around an outer surface of at least one of the legs, the groove having a downwardly facing upper surface and an upwardly facing lower surface, and a second recess formed on the outer surface of the at least one of the legs that extends radially inwardly closer to the central axis than the groove is to the central axis, the second recess having a downwardly facing upper surface and an upwardly facing lower surface. The groove and the second recess are respectively configured to facilitate engagement by two different instruments to the receiving part.

19 Claims, 6 Drawing Sheets

(56)                References Cited

U.S. PATENT DOCUMENTS

| | | | |
|---|---|---|---|
| 11,191,573 B1* | 12/2021 | Leff | A61B 17/7037 |
| 11,369,417 B1* | 6/2022 | Linder | A61B 17/7032 |
| 11,464,545 B1* | 10/2022 | Pandya | A61B 17/7032 |
| 11,490,931 B2 | 11/2022 | Casey et al. | |
| 11,627,996 B2 | 4/2023 | Jackson | |
| 11,812,999 B2* | 11/2023 | Biedermann | A61B 17/7032 |
| 2007/0270860 A1* | 11/2007 | Jackson | A61B 17/702 |
| | | | 606/326 |
| 2008/0200956 A1* | 8/2008 | Beckwith | A61B 17/7032 |
| | | | 606/301 |
| 2009/0105769 A1* | 4/2009 | Rock | A61B 17/7038 |
| | | | 606/301 |
| 2012/0209336 A1* | 8/2012 | Jackson | A61B 17/7032 |
| | | | 606/305 |
| 2012/0310284 A1* | 12/2012 | Gerchow | A61B 17/7037 |
| | | | 606/264 |
| 2013/0060293 A1* | 3/2013 | Jackson | A61B 17/7037 |
| | | | 606/305 |
| 2013/0066380 A1* | 3/2013 | Haskins | A61B 17/8685 |
| | | | 606/305 |
| 2013/0110177 A1* | 5/2013 | Doubler | A61B 17/7037 |
| | | | 606/305 |
| 2013/0131730 A1* | 5/2013 | Jackson | A61B 17/7032 |
| | | | 606/278 |
| 2013/0197586 A1* | 8/2013 | Matthis | A61B 17/7035 |
| | | | 606/279 |
| 2014/0188175 A1* | 7/2014 | Mishra | A61B 17/7037 |
| | | | 606/279 |
| 2014/0321945 A1* | 10/2014 | Black | F16B 29/00 |
| | | | 411/383 |
| 2015/0112390 A1* | 4/2015 | Fang | A61B 17/7037 |
| | | | 606/279 |
| 2015/0182265 A1* | 7/2015 | Biedermann | A61B 17/7032 |
| | | | 606/265 |
| 2016/0143665 A1* | 5/2016 | Biedermann | A61B 17/7037 |
| | | | 606/267 |
| 2016/0361093 A1* | 12/2016 | Biedermann | A61B 17/7032 |
| 2017/0311988 A1* | 11/2017 | Petit | A61B 17/7038 |
| 2018/0325558 A1* | 11/2018 | Yacoub | A61B 17/7056 |
| 2019/0008562 A1* | 1/2019 | Melton | A61F 2/442 |
| 2019/0059957 A1* | 2/2019 | Heuer | A61B 17/7083 |
| 2019/0142470 A1* | 5/2019 | Kim | A61B 17/708 |
| | | | 606/246 |
| 2019/0254724 A1* | 8/2019 | McClintock | A61B 17/8665 |
| 2020/0038075 A1* | 2/2020 | Barrus | A61B 17/7037 |
| 2020/0054366 A1* | 2/2020 | Ark | A61B 17/8685 |
| 2020/0352609 A1* | 11/2020 | Heuer | A61B 17/7037 |
| 2020/0367944 A1* | 11/2020 | Loftis | A61B 17/7034 |
| 2021/0015521 A1* | 1/2021 | Biedermann | A61B 17/7032 |
| 2021/0030445 A1* | 2/2021 | Avidano | A61B 17/8605 |
| 2021/0259742 A1* | 8/2021 | Biedermann | A61B 17/7035 |
| 2021/0282819 A1* | 9/2021 | Biedermann | A61B 17/7038 |
| 2022/0280199 A1* | 9/2022 | Chen | A61B 17/7067 |
| 2022/0280201 A1* | 9/2022 | Mickiewicz | A61B 17/862 |
| 2022/0280207 A1* | 9/2022 | Biester | A61B 17/7086 |
| 2022/0395298 A1* | 12/2022 | Shoshtaev | A61B 17/7032 |
| 2023/0225766 A1* | 7/2023 | Gray | A61B 17/8685 |
| | | | 606/267 |
| 2023/0225777 A1* | 7/2023 | Lomeli | A61B 17/865 |
| | | | 206/343 |
| 2023/0301689 A1* | 9/2023 | Allen | A61B 17/7037 |
| 2024/0081868 A1* | 3/2024 | Peterson | A61B 17/7032 |
| 2024/0423679 A1* | 12/2024 | Larosa | A61B 17/7032 |

FOREIGN PATENT DOCUMENTS

| | | |
|---|---|---|
| WO | WO 2018/191131 A1 | 10/2018 |
| WO | WO 2023/022886 A2 | 2/2023 |

\* cited by examiner

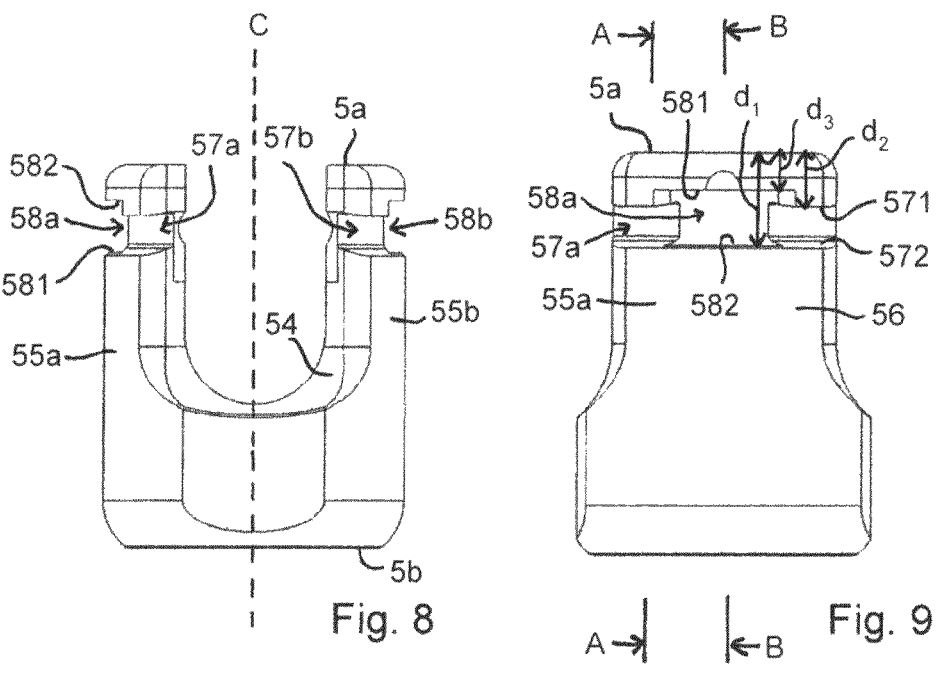
Fig. 8
Fig. 9
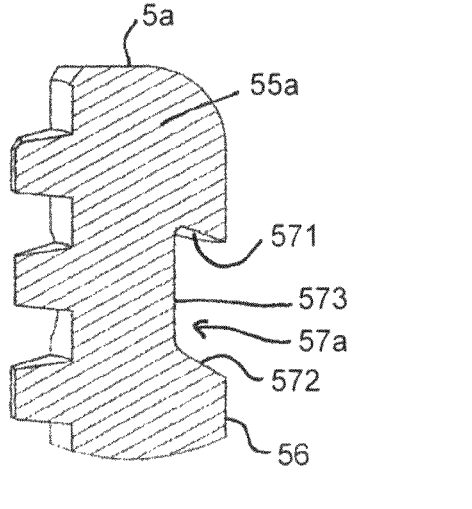
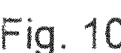
Fig. 10
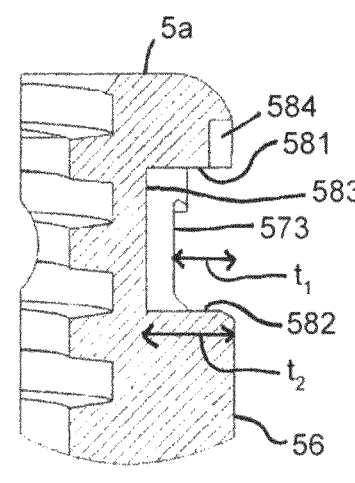
Fig. 11

RECEIVING PART OF A BONE ANCHORING DEVICE AND SYSTEM INCLUDING THE RECEIVING PART AND AT LEAST ONE INSTRUMENT

CROSS-REFERENCE TO RELATED APPLICATION(S)

The present application claims priority to and the benefit of U.S. Provisional Patent Application No. 63/678,208, filed Aug. 1, 2024, the contents of which are hereby incorporated by reference in their entirety, and claims priority from European Patent Application EP 24 192 465.3, filed Aug. 1, 2024, the contents of which are hereby incorporated by reference in their entirety.

BACKGROUND

Field

The present application relates to a receiving part that may be part of a coupling device for coupling a bone anchoring element to a stabilization element such as a rod. In particular, the receiving part may be configured to interchangeably engage a first instrument and a second instrument different from the first instrument, in particular, for use in spinal surgery. The present application further relates to a coupling device including such a receiving part, and to a system including such a receiving part and at least one instrument.

Description of Related Art

A receiving part of a bone anchoring device is known from US 2016/0361093 A1, the receiving part including a substantially U-shaped recess that forms two free legs. A groove is provided in an outer surface of each of the legs, wherein in a plane that includes the central axis of the receiving part and that extends through a center of each leg, a contour of a surface of the groove has at least a first arcuate portion and a second arcuate portion opposing the first arcuate portion, and the contour is substantially free from straight portions.

Various other receiving parts with different engagement structures for instruments are known, for example, from WO 2018/191131 A1 or WO 2023/022886 A2.

SUMMARY

It is an object of the present invention to provide an improved receiving part for a bone anchoring device, and a coupling device including such a receiving part that can, in particular, facilitate and/or support engagement of the receiving part with an instrument, and wherein at least two different instruments can be used selectively and interchangeably with the receiving part. Furthermore, it is an object of the present invention to provide a system including such a receiving part and at least one instrument.

According to an embodiment, a receiving part of a bone anchoring device is provided, the receiving part having a central axis that extends from a first end to a second end, wherein a substantially U-shaped-recess is provided adjacent to the first end for receiving a rod, the substantially U-shaped recess forming two free legs of the receiving part. The receiving part has a circumferential groove in an outer surface of at least one of the legs, the groove being delimited in a direction of the central axis by an upper surface and a lower surface, and a recess in the outer surface of the at least one leg, the recess being delimited in the direction of the central axis by an upper surface and a lower surface. At the outer surface of the receiving part, the lower surface of the recess and the lower surface of the groove are provided at substantially the same distance from the first end of the receiving part.

The groove and/or the recess may serve to facilitate engagement by an instrument with the receiving part. The respective upper and lower surfaces of the groove and the recess can provide for safe attachment of the instrument with the receiving part, and can in particular allow a force to be transmitted from the instrument onto the receiving part, while preventing inadvertent detachment of the instrument from the receiving part.

By providing the lower surfaces of both the recess and the groove at the same axial height of the receiving part at its outer surface, a reproducible position of an instrument attached to the receiving part may be provided, even when using different instruments. Moreover, by providing both lower surfaces at the same axial height at the outer surface, it can be ensured that when using an instrument that engages only one of the groove or the recess, a coupling process of attaching the instrument to the receiving part is not interfered by the other one of the groove or the recess.

The receiving part can be manufactured in an easy and cost-efficient manner. Moreover, the receiving part may be used with different instruments that differ with respect to their engagement structures for engaging the receiving part. Specifically, a first instrument may be configured for engagement with the groove of the receiving part, and a second instrument may be configured for engagement with the recess of the receiving part. The first instrument may be configured to only engage the groove and not the recess, whereas the second instrument may be configured to only engage the recess and not the groove.

Hence, the receiving part may be combined with existing instruments of different types, which can increase the versatility of the receiving part. This may also reduce the costs of the inventory necessary for surgery.

A bone anchoring device including the receiving part and a bone anchoring element may be configured in any suitable form. For example, the bone anchoring device can be a polyaxial bone anchoring device, a monoplanar bone anchoring device, or a monoaxial bone anchoring device. The bone anchoring device may be of a bottom-loading type, in which a head of the bone anchoring element is insertable from the bottom end into the receiving part, or may be of a top-loading type, in which the head is insertable from the top end into the receiving part.

According to a further embodiment, a coupling device is provided for coupling a bone anchoring element to a rod, the bone anchoring element including a shank for anchoring in bone, wherein the coupling device includes the receiving part according to the above embodiments. Preferably, the bone anchoring element includes a head, and the receiving part is configured to receive the head of the bone anchoring element, wherein further preferably the coupling device includes a locking device configured to cooperate with the receiving part to lock the head in the receiving part.

According to a still further embodiment, a system including at least one instrument and a receiving part according to the above embodiments is provided, wherein the instrument includes a tubular portion having two arms, wherein at least one arm includes at its inner surface at least one protrusion configured to engage the groove and/or the recess of the receiving part. Preferably, the instrument is a first instrument and the at least one protrusion is formed as a circumferentially extending rib configured to engage the groove of the receiving part, and/or the instrument is a second instrument and the at least one protrusion is formed in a middle portion of the arm in a circumferential direction of the second instrument and configured to engage the recess of the receiving part.

The receiving part, the coupling device, and the system may each be used in particular in spinal surgery, and more specifically in minimally invasive surgery (MIS).

BRIEF DESCRIPTION OF THE DRAWINGS

Further features and advantages of the invention will become apparent from the description of embodiments by means of the accompanying drawings. In the drawings:

FIG. 8 shows a side view of the receiving part of FIGS. 1 to 7.

FIG. 9 shows another side view of the receiving part of FIGS. 1 to 8.

FIG. 10 shows an enlarged cross-sectional view of a detail of the receiving part of FIGS. 1 to 9, the cross-section taken along line A-A in FIG. 9.

FIG. 11 shows an enlarged cross-sectional view of a detail of the receiving part of FIGS. 1 to 10, the cross-section taken along line B-B in FIG. 9.

DETAILED DESCRIPTION

Figure 1:
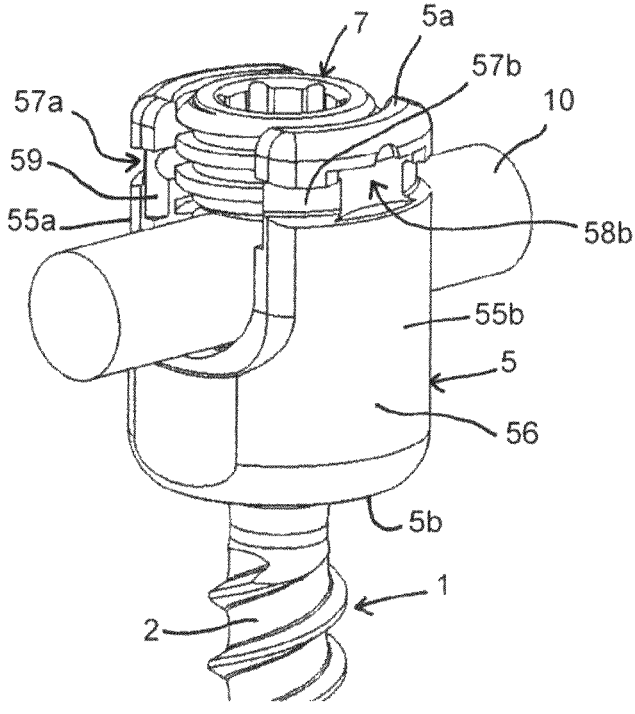
FIG. 1 shows a perspective view of a bone anchoring device including a receiving part according to a first embodiment of the invention.
Figure 2:
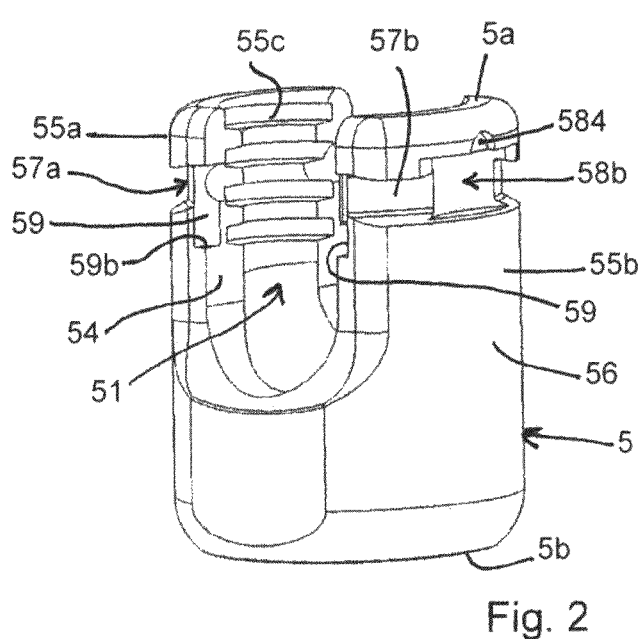
FIG. 2 shows a perspective view of the receiving part of FIG. 1.
Figures 3, 4, 5, 6, 7:
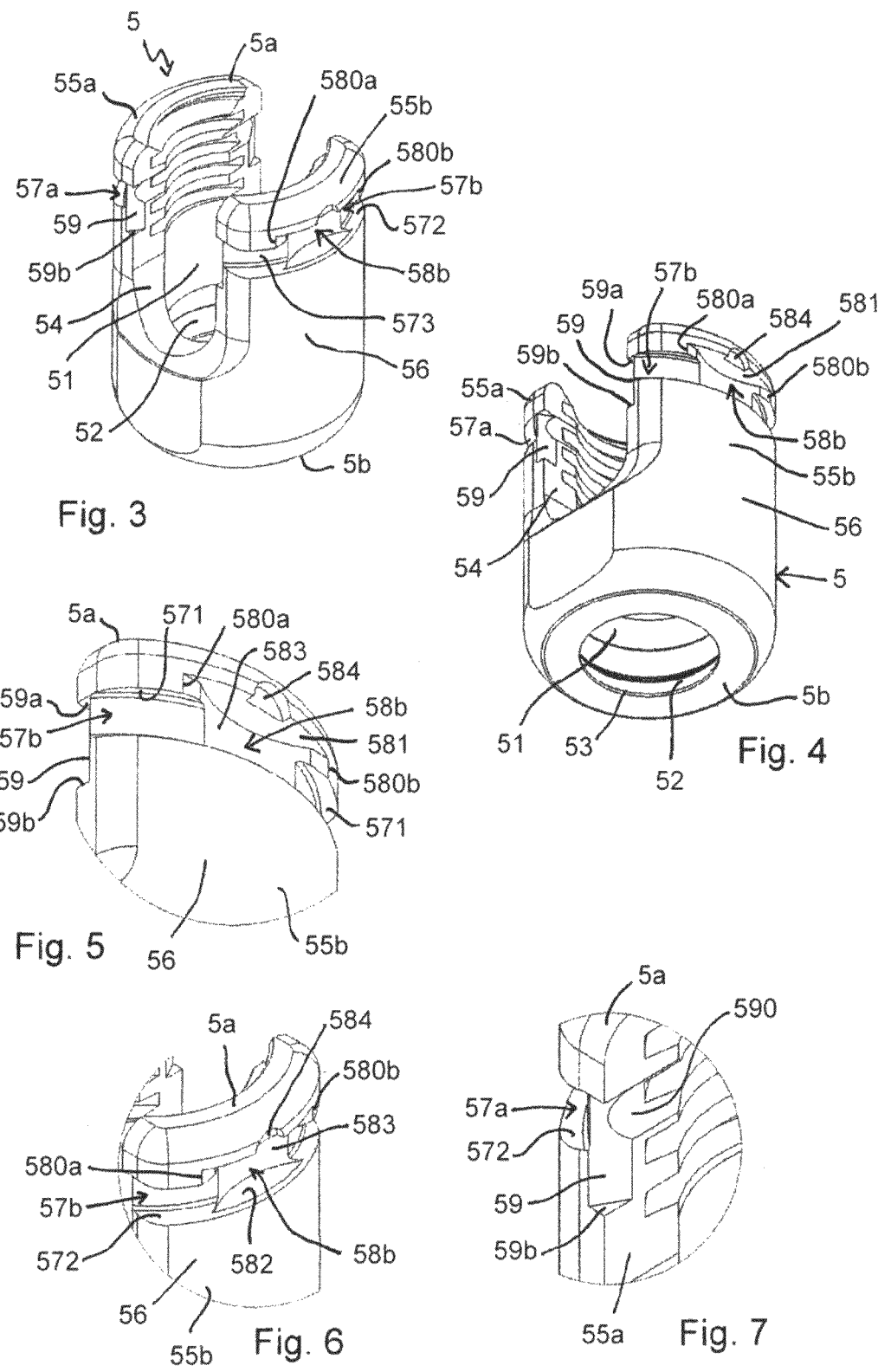
FIG. 3 shows a perspective view from above the receiving part of FIGS. 1 and 2.
FIG. 4 shows a perspective view from below the receiving part of FIGS. 1 to 3.
FIG. 5 shows an enlarged view of a portion of the receiving part shown in FIG. 4.
FIG. 6 shows an enlarged view of a portion of the receiving part shown in FIG. 3.
FIG. 7 shows an enlarged view of another portion of the receiving part shown in FIG. 3.
Figures 12, 13, 14:
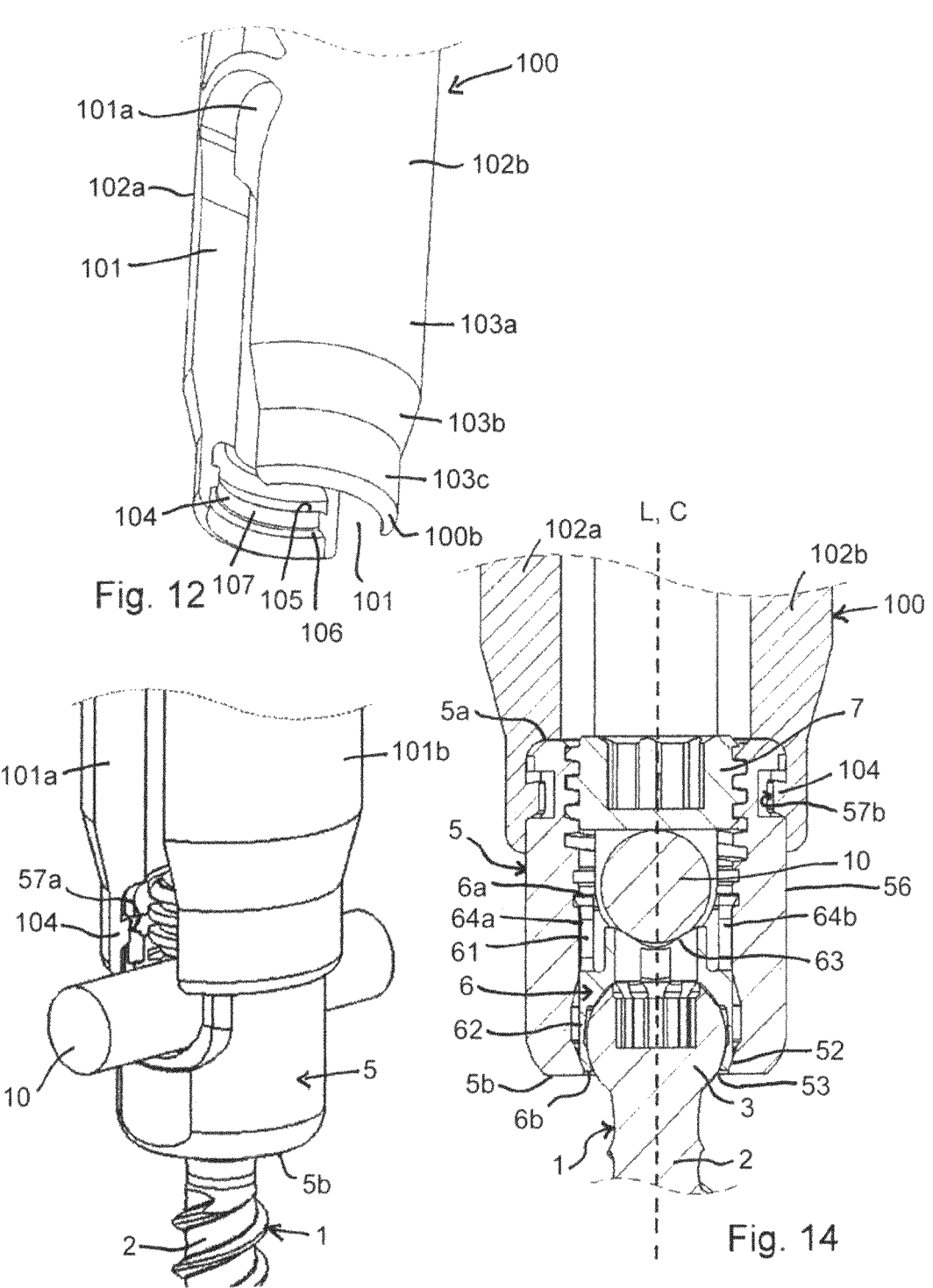
FIG. 12 shows a perspective view of a portion of an instrument according to a first embodiment.
FIG. 13 shows a perspective view of the bone anchoring device of FIG. 1 with a portion of the instrument of FIG. 12 attached thereto.
FIG. 14 shows a cross-sectional view of the bone anchoring device with the portion of the instrument shown in FIG. 13, the cross-section taken in a plane perpendicular to a rod axis of an inserted rod.
Figures 15, 16, 17:
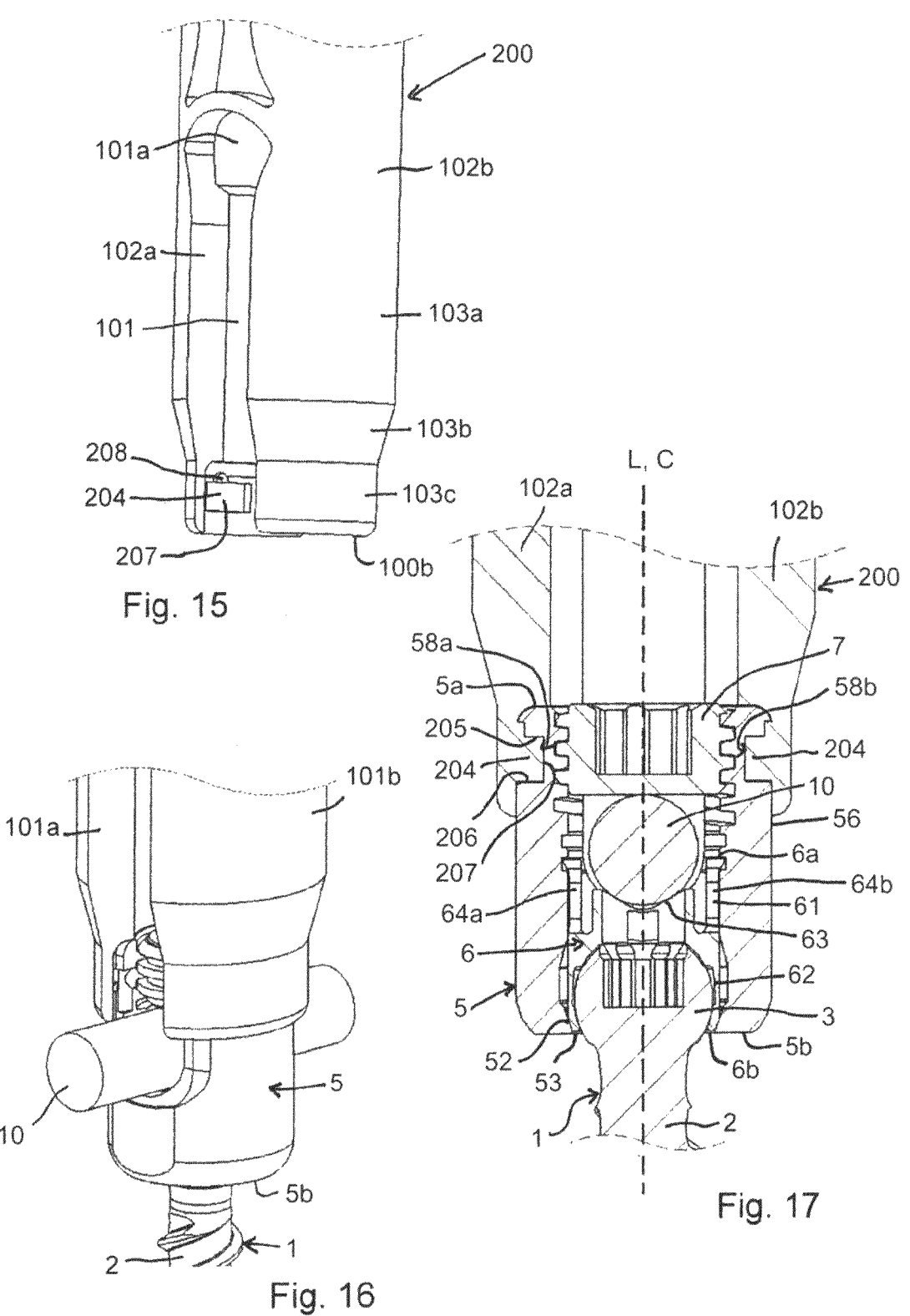
FIG. 15 shows a perspective view of a portion of an instrument according to a second embodiment.
FIG. 16 shows a perspective view of the bone anchoring device of FIG. 1 with a portion of the instrument of FIG. 15 attached thereto.
FIG. 17 shows a cross-sectional view of the bone anchoring device with the portion of the instrument shown in FIG. 16, the cross-section taken in a plane perpendicular to a rod axis of an inserted rod.

As shown in FIG. 1, and with additional reference to FIGS. 14 and 17, a bone anchoring device according to a first embodiment includes a bone anchoring element 1 with a threaded shank 2 and a head 3 with a spherical outer surface portion. The bone anchoring device further includes a receiving part 5 for coupling the bone anchoring element 1 to a spinal fixation element, for example, a rod 10. A pressure element 6 is provided at least partially within the receiving part 5, the pressure element 6 being configured to exert pressure onto the inserted head 3 to lock the head 3 in the receiving part 5. A fixation member, for example, a set screw 7, is provided for fixing the rod 10 in the receiving part 5. The pressure element 6 and the head 3 are shown in FIGS. 14 and 17.

The receiving part 5 is shown in more detail in FIGS. 2 to 11. The receiving part 5 may be a monolithic part. Typically, the receiving part 5 may be formed as a substantially cylindrical part with a first end or top end 5a, a second end or bottom end 5b, and a central axis C extending through the top end 5a and the bottom end 5b. A passage 51 extends from the top end 5a to the bottom end 5b along the central axis C. Close to the bottom end 5b of the receiving part 5, a narrowing portion 52 in the passage 51 may provide a seat for the head 3 of the anchoring element 1. At the bottom end 5b of the receiving part 5, a lower opening 53 is formed that permits the shank 2 to extend therethrough. The receiving part 5 further defines a substantially U-shaped recess 54 that extends from the top end 5a in a direction towards the bottom end 5b. The U-shaped recess 54 serves for receiving the rod 10 therein. Two free legs 55a, 55b of the receiving part 5 are formed by the U-shaped recess 54. In an upper portion of the legs 55a, 55b, an internal thread 55c may be provided for cooperating with the set screw 7 for fixing the rod 10 relative to the receiving part. The receiving part 5 may have rounded edges at its top end 5a.

On an outer surface 56 of each of the legs 55a, 55b, a circumferential groove 57a, 57b and a recess 58a, 58b are formed, respectively. The circumferential grooves 57a, 57b and/or the recesses 58a, 58b may serve as engagement portions for engagement by an instrument with the receiving part 5, as explained in more detail below. More generally, the recesses 58a, 58b each forms a notch that intersects the corresponding groove 57a, 57b.

The circumferential grooves 57a, 57b and the recesses 58a, 58b each extends radially inwardly from the outer surface 56 of the receiving part 5 towards the central axis C. Thus, the thickness of the legs 55a, 55b in the radial direction may be reduced by the grooves 57a, 57b and by the recesses 58a, 58b. At each of the legs 55a, 55b, the respective circumferential groove 57a, 57b and the respective recess 58a, 58b intersect each other at or near the center of the leg in the circumferential direction.

The circumferential groove 57a, 57b of each leg 55a, 55b is provided at a distance from the top end 5a of the receiving part 5. Moreover, the circumferential grooves 57a, 57b extend circumferentially from one end of the channel formed by the U-shaped recess 54 to the opposite end of the channel, and are open towards the U-shaped recess 54. In other words, the circumferential grooves 57a, 57b extend in a circumferential direction of the receiving part 5, e.g., in a plane perpendicular to the central axis C, in an arcuate shape along the entire circumferential extension of the respective leg 55a, 55b.

Each of the circumferential grooves 57a, 57b is delimited towards the upper end 5a of the receiving part 5 by an upper surface 571 of the groove, and is delimited towards the bottom end 5b by a lower surface 572 of the groove. As can best be seen in FIG. 9, at the outer surface 56 of the receiving part 5, the lower surface 572 of the groove 57a, 57b is provided at a first distance $d_1$ from the top end 5a of the receiving part 5, and the upper surface 571 is provided at a second distance $d_2$ from the top end 5a of the receiving part 5, the second distance $d_2$ being smaller than the first distance $d_1$.

The upper surface 571 and the lower surface 572 of the groove 57a, 57b may be inclined from the outer surface 56 of the receiving part, e.g., to extend towards the top end 5a as the upper and lower surfaces extend radially inwardly. In the present embodiment, the upper surface 571 and the lower surface 572 are substantially flat or planar faces that extend, e.g., conically, from the outer surface 56 radially inwardly into the receiving part 5 in a depth direction thereof. A sidewall 573 or bottom of the groove 57a, 57b delimits the groove in the depth direction. The sidewall 573 may be generally flat or planar and may provide a generally cylindrical surface that connects to the upper and lower surfaces 571, 572 at rounded edges.

It shall be understood that the upper and lower surfaces 571, 572, as well as the sidewall 573, are not limited to flat or planar faces. Rather, they can have any other shape, such as a rounded or arcuate shape. Depending on the shape of the upper and lower surfaces 571, 572, the sidewall 573 may also be omitted, for example, if the upper and lower surfaces connect directly with one another.

The grooves 57a, 57b have a depth $t_1$ extending from the outer surface 56 of the receiving part 5 to a point of the groove extending furthest radially inwards into the receiving part. In the present embodiment, the grooves 57a, 57b have the depth $t_1$ between the outer surface 56 and the sidewall 573, as depicted in FIGS. 10 and 11.

The recess 58a, 58b of each leg 55a, 55b is provided in the middle of the respective leg in the circumferential direction. In the axial direction, the recesses 58a, 58b are located at a distance from the top end 5a of the receiving part. In the circumferential direction of the respective leg 55a, 55b, the recess 58a, 58b extends from a first end 580a to a second end 580b, as can be seen in particular in FIGS. 4 to 6. A width of the recesses 58a, 58b between the first end 580a and the second end 580b is smaller than the circumferential extension of the grooves 57a, 57b. In the outer surface 56 of the receiving part, a contour of each of the recesses 58a, 58b may have a substantially rectangular shape.

Each of the recesses 58a, 58b is delimited towards the upper end 5a of the receiving part 5 by an upper surface 581, and is delimited towards the bottom end 5b by a lower surface 582. As can best be seen in FIG. 9, at the outer surface 56 of the receiving part 5, the lower surface 582 of each of the recesses 58a, 58b is provided at substantially the same first distance $d_1$ from the top end 5a of the receiving part 5 as the lower surface 572 of the respective groove 57a, 57b. In particular, the lower surface 582 of the recesses 58a, 58b may be flush with the lower surface 572 of the grooves 57a, 57b.

The upper surface 581 of the recesses 58a, 58b is provided at a third distance $d_3$ from the top end 5a of the receiving part 5, wherein the third distance $d_3$ may be smaller than the second distance $d_2$ between the upper surface 571 of the grooves 57a, 57b and the top end 5a of the receiving part 5. By means of the upper surface 581 and the lower surface 582, the recesses 58a, 58b are closed towards both the top end 5a and the bottom end 5b of the receiving part.

The upper surface 581 and the lower surface 582 of the recesses 58a, 58b may extend substantially perpendicular to the central axis C in a direction from the outer surface 56 of the receiving part towards the central axis C, i.e., radially inwardly towards the passage 51. In the present embodiment, the upper surface 581 and the lower surface 582 are substantially planar faces that extend from the outer surface 56 into the receiving part 5 in a depth direction thereof. A sidewall 583 or bottom of the recesses 58a, 58b delimits the recesses in the depth direction.

The recesses 58a, 58b have a maximum depth $t_2$ measured from the outer surface 56 of the receiving part 5 to a point of the recesses extending furthest radially inwards into the receiving part 5. The sidewall 583 of the recesses 58a, 58b may have a curved (e.g., concave) shape that extends radially inwardly from each end 580a, 580b of the recesses inwards into the receiving part. Preferably, the shape of the sidewall 583 is cylindrical, with the cylinder axis being substantially parallel to the central axis C.

As can be seen from FIG. 11, the maximum depth $t_2$ of the recesses 58a, 58b exceeds or is greater than the depth $t_1$ of the grooves 57a, 57b.

It shall be understood that the upper and lower surfaces 581, 582 and the sidewall 583 of the recesses 58a, 58b are not limited in their shape to the respective planar faces and curved shape of the present embodiment. Rather, they can have any other shape, for example, the upper and lower surfaces can have a rounded or arcuate shape, and/or the sidewall 583 can have a planar shape. Depending on the shape of the upper and lower surfaces 581, 582, the sidewall 583 may also be omitted, e.g., if the upper and lower surfaces are inclined towards one another or have a rounded or arcuate shape so that they meet and directly connect at their positions furthest away from the outer surface 56 (not shown in the figures).

The recesses 58a, 58b may further have a notch 584 provided in the outer surface 56 of the receiving part that extends from the upper surface 582 of the recesses 58a, 58b towards the upper end 5a of the receiving part. The notch 584 may be located circumferentially at or near the middle of the recesses 58a, 58b between its two ends 580a, 580b, and may have a curved shape. A depth of the notch 584 may be smaller than the depth of the recesses 58a, 58b and the depth of the grooves 57a, 57b.

Preferably, the groove 57a and recess 58a provided on a first leg 55a of the receiving part are arranged and formed to be symmetrical with respect to the groove 57b and recess 58b of the second leg 58b, relative to a plane that includes the central axis C and that passes centrally through the U-shaped recess 54 of the receiving part 5.

In addition, the legs 55a, 55b may have cutouts 59 at each circumferential end of each leg 55a, 55b that are facing or directed towards the substantially U-shaped recess 54. Each cutout 59 may extend in an axial direction from a first end 59a of the cutout 59 that is located at or axially corresponding to the upper surface 571 of the grooves 57a, 57b, to a second end 59b of the cutout 59 that is located closer to the bottom end 5b of the receiving part 5 than the lower surface 572 of the grooves 57a, 57b is to the bottom end of the receiving part.

In addition, a bevelled surface 590 may be provided that is located below the upper surface 571 of each groove 57a, 57b and extends from each cutout 59 radially inwardly towards the internal thread 55c. The bevelled surface 590 may facilitate insertion of a portion of an instrument into the inside of the receiving part 5, e.g., generally into passage 51.

The pressure element 6, that can best be seen in the cross-sectional view of FIGS. 14 and 17, may include a substantially cylindrical first portion 61 at an upper end 6a of the pressure element 6, and a substantially cylindrical second portion 62 at a lower end 6b thereof. The substantially cylindrical second portion 62 may be configured to extend at least partially around an inserted head 3, and may be at least partially flexible to clamp the inserted head. For example, the second portion 62 may have a plurality of longitudinal slits (not shown in the figures) that render the second portion 62 flexible. Clamping of the inserted head 3 may be achieved by moving the pressure member 6 downwards within the passage 51 of the receiving part 5 so that the second portion 62 of the pressure member 6 is compressed by the narrowing portion 52 of the receiving part 5.

The first portion 61 of the pressure element 6 may include a base 63 having a substantially V-shaped or U-shaped contour, which forms a rod support surface for an inserted rod, and two upstanding legs 64a, 64b at both sides of the base 63. An upper end of the legs 64a, 64b may provide for a stop that cooperates with the receiving part to prevent or restrict upward movement of the pressure element 6 within the receiving part 5.

A coupling device according to an embodiment of the invention, which serves for coupling a bone anchoring element 1 to a rod 10, may include the receiving part 5 for receiving the rod 10 and the head 3 of the bone anchoring element 1 therein, and a locking device in the form of the pressure element 6 that is configured to exert pressure onto the head 3 to lock the head 3 in the receiving part 5. The coupling device together with the bone anchoring element may, for example, form a polyaxial bone anchoring device where the shank can pivot relative to the receiving part, and/or a monoplanar bone anchoring device where the pivoting motion of the shank relative to the receiving part is restricted to a single plane, and/or a monoaxial bone anchoring device where the shank can assume a single predetermined pivoting angle with respect to the receiving part and where rotation between the shank and the receiving part may or may not be possible. The bone anchoring device may be of a bottom-loading type in which the head is insertable from the bottom end 5b into the receiving part, or of a top-loading type in which the head is insertable from the top end 5a into the receiving part.

The receiving part can have other shapes than those shown in the described embodiments. In particular, the receiving part can have any shape that permits receiving of the head of the bone anchoring device in a pivotable manner. Also, the receiving part can have a structure which allows pivoting of the bone anchoring element to one side at a greater angle than to another side. For monoaxial coupling devices, the receiving part can be fixedly or otherwise monoaxially connected to the shank, or can be monolithically formed with a shank, thereby omitting a head.

The pressure element can also have other shapes than those shown in the described embodiments. The pressure element 6 of the embodiments described above is a monolithic part. However, the pressure element may be formed with two or more parts that are configured to cooperate with one another to lock the head in the receiving part. The pressure element can also only cover or contact the inserted head from above, where the head can pivot in a seat provided directly on the receiving part (i.e., the head can directly engage the receiving part). Instead of a pressure element, any other locking device configured to lock the head in the receiving part can also be implemented, such as an outer ring that is at least partially arranged around a head receiving portion of the receiving part and configured to exert a clamping force onto the head receiving portion to lock an inserted head therein.

Parts and portions of the receiving part and the coupling device in general may be made of any material, preferably, however, of a bio-compatible material, such as titanium or stainless steel, or of any other bio-compatible metal or metal alloy, or plastic material. For bio-compatible alloys, a Ni—Ti alloy, for example Nitinol, may be used. Other materials that can be used are, for example, Magnesium or Magnesium alloys, and bio-compatible plastic materials that can be used may be for example, Polyether ether ketone (PEEK) or Poly-L-lactide acid (PLLA). The parts can be made of the same or of different materials from one another.

Next, an instrument according to a first embodiment, which is configured to engage the receiving part 5, will be described, with additional reference to FIGS. 12 to 14. This instrument embodiment is an example of an instrument configured to engage the grooves 57a, 57b. In the figures, only a lower part of a tubular portion 100 of the instrument is shown. Specifically, the tubular portion 100 of the instrument extends from an upper end (not shown in the figures) to a second end 100b along a longitudinal axis L. The tubular portion 100 may be substantially cylindrical in shape.

Two longitudinal slits 101 are provided in the tubular portion 100 that are open towards the second end 100b and that extend from the second end 100b in the direction of the longitudinal axis L. Each slit may terminate in an enlarged portion 101a at a distance from the second end 100b. By means of the slits 101, two arms 102a, 102b of the tubular portion 100 are formed. The slits 101 render the tubular portion at least partially flexible, so that the arms 102a, 102b are expandable away from each other and compressible towards each other.

An outer diameter of the tubular portion 100 may decrease towards the second end 100b. For example, in the present embodiment, the tubular portion 100 of the instrument includes a first cylinder-segment shaped portion 103a and a second cylinder-segment shaped portion 103c adjacent the second end 100b, wherein an outer diameter of the second cylinder-segment shaped portion 103c is smaller than an outer diameter of the first cylinder-segment shaped portion 103a. The outer diameter may gradually decrease from the first cylinder-segment shaped portion to the second cylinder-segment shaped portion to form an intermediate narrowing portion 103b.

An inner diameter of the tubular portion 100 is such that the arms smoothly fit around the outer surface 56 of the receiving part to engage the receiving part therebetween.

At an inner surface of the second cylinder-segment shaped portion 103c, a circumferentially extending rib 104 is provided at each arm 102a, 102b which is configured to engage the circumferential groove 57a, 57b provided at the outer surface 56 of the arms 55a, 55b of the receiving part 5.

Specifically, the circumferential rib 104 may have an upper surface 105 and a lower surface 106 respectively delimiting the rib towards the first end (not shown) and the second end 100b of the tubular portion 100, and a sidewall 107 connecting the upper and lower surfaces 105, 106 of the rib. The upper and lower surfaces 105, 106 may be inclined with respect to the longitudinal axis L, and are formed such that the ribs 104 fit into the grooves 57a, 57b, respectively. In greater detail, the upper and lower surfaces 105, 106 are configured to respectively abut on or against the upper and lower surfaces 571, 572 of the groove 57a, 57b, and the sidewall 107 of the circumferential rib 104 may abut on the sidewall 573 of the grooves 57a, 57b when the tubular portion 100 is attached to the receiving part 5.

The circumferential rib 104 may extend along an entire width of the respective arm 102a, 102b in the circumferential direction thereof.

In use, the tubular portion 100 of the instrument is advanced with its second end 100b towards the upper end 5a of the receiving part 5 to place the tubular portion onto the receiving part. Further advancement of the tubular portion 100 towards the bottom end 5b of the receiving part spreads the arms 102a, 102b of the tubular portion apart. The rounded edges of the receiving part at its top end 5a may facilitate and assist in spreading the arms of the tubular portion 100. Finally, the circumferential ribs 104 provided at the inner surfaces of the arms 102a, 102b snap into the circumferential grooves 57a, 57b of the respective legs 55a, 55b of the receiving part 5, which causes the arms 102a, 102b to compress again to thus couple the tubular portion 100 to the receiving part 5.

Alternatively, for attaching the tubular portion 100 to the receiving part 5, the tubular portion 100 can be advanced towards the receiving part with its arms 102a, 102b located circumferentially at the position of the substantially U-shaped-recess 54 of the receiving part, i.e., circumferentially between the legs 55a, 55b of the receiving part 5. When the circumferential ribs 104 are located axially at the position of the circumferential grooves 57a, 57b, the tube 100 can be rotated around its longitudinal axis L so that the circumferential ribs 104 enter the circumferential grooves 57a, 57b from the side instead.

A second embodiment of an instrument configured to engage the receiving part 5 will now be described, with additional reference to FIGS. 15 to 17. This instrument embodiment is an example of an instrument configured to engage the recesses 58a, 58b of the receiving part. In the figures, only a lower part of a tubular portion 200 of the instrument is shown. The tubular portion 200 of the second instrument is in some respects similar to the tubular portion 100 of the first instrument described above, and in the figures, similar features and elements are denoted by the same reference numbers. In the following description, only the differences of the second instrument from the first instrument will therefore be described.

Instead of the circumferential rib 104 of the tubular portion 100 of the first instrument, the tubular portion 200 of the second instrument includes, at an inner surface of the second cylinder-segment shaped portion 103c, a protrusion 204 provided at each arm 102a, 102b that is configured to engage the recesses 58a, 58b provided at the outer surface 56 of the receiving part 5.

The protrusion 204 may be formed at or near a middle portion of the respective arm 102a, 102b in a circumferential direction thereof. In the circumferential direction of the arms, the protrusion 204 may extend along a length that is equal to or only slightly smaller than the width of the recesses 58a, 58b of the receiving part 5 measured between the first end 580a and the second end 580b. A contour of the protrusion 204 when viewed in a plane that extends through the inner surface of the arms may have a substantially rectangular shape.

The protrusion 204 may have an upper surface 205 and a lower surface 206 respectively delimiting the protrusion towards the first end (not shown) and the second end 100b of the tubular portion 200, and a sidewall 207 connecting the upper and lower surfaces 205, 206. The upper and lower surfaces 205, 206 may be substantially planar and extend substantially perpendicular to the longitudinal axis L. The sidewall 207 may have a curved shape that is complementary to the curved shape of the sidewall 583 of the recesses

58a, 58b provided at the receiving part 5. A thickness of the protrusion 204 between the inner surface of the respective arm 102a, 102b and the sidewall 207 may be substantially equal to the depth of the recesses 58a, 58b. More generally, the shape of the protrusion 204 may be such that the protrusion can engage the recesses 58a, 58b. In greater detail, the upper and lower surfaces 205, 206 of the protrusion 204 may be formed and arranged such that they respectively abut against the upper and lower surfaces 581, 582 of the recesses 58a, 58b, and the sidewall 207 of the protrusion 204 may abut against the sidewall 583 of the recesses 58a, 58b when the tubular portion 200 is attached to the receiving part 5. However, the protrusion 204 may not be configured to engage portions of the grooves 57a, 57b that extend circumferentially away from the recesses 58a, 58b.

The protrusion 204 may further include a projection 208 that is shaped and arranged to engage the notch 584 of the recesses 58a, 58b provided in the outer surface 56 of the receiving part 5 when the protrusion 204 engages the recesses 58a, 58b.

Figures 18, 19:
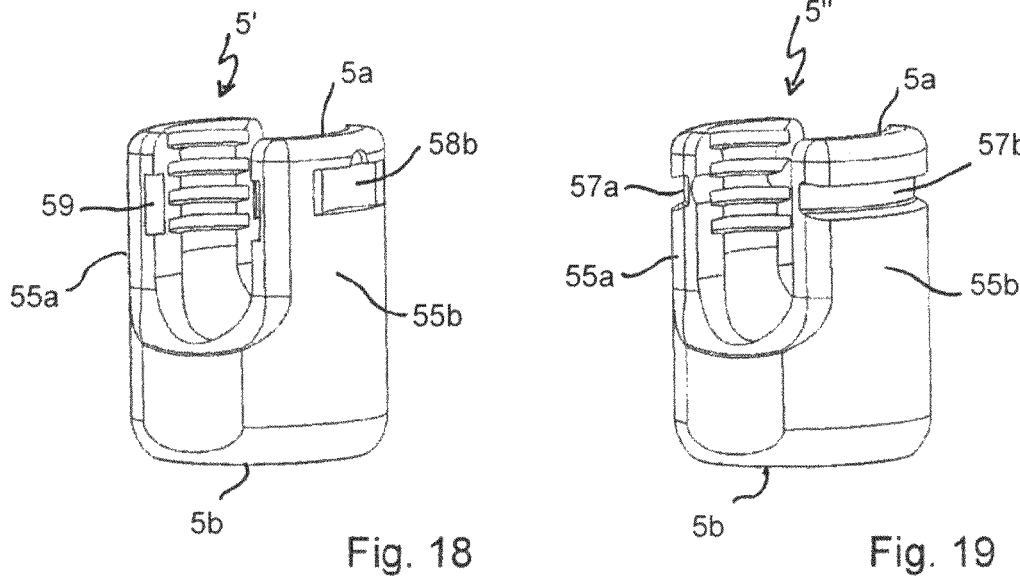
FIG. 18 shows a perspective view of a receiving part according to a second embodiment.
FIG. 19 shows a perspective view of a receiving part according to a third embodiment.

In an example of another receiving part 5' according to a second embodiment shown in FIG. 18, the receiving part is provided without the circumferential grooves 57a, 57b or the bevelled surfaces 590 at the legs 55a, 55b. Hence, the receiving part 5' shown in FIG. 18 only includes the recesses 58a, 58b and the cutouts 59 provided at its legs 55a, 55b, and the receiving part 5' may be used together with the second instrument described above with reference to FIGS. 15 to 17.

In an example of yet another receiving part 5" according to a third embodiment shown in FIG. 19, the receiving part is provided without the recesses 58a, 58b or the cutouts 59 at the legs 55a, 55b. Hence, the receiving part 5" shown in FIG. 19 only includes the circumferential grooves 57a, 57b and the bevelled surfaces 590 provided at its legs 55a, 55b, and the receiving part 5" may be used together with the first instrument described above with reference to FIGS. 12 to 14.

Thus, the receiving part 5 according to embodiments of the invention shown in FIGS. 1 to 17 can be used with two instrument types, one of which is configured to engage a receiving part 5' as shown in FIG. 18, and another of which is configured to engage a receiving part 5" as shown in FIG. 19. While not explicitly described, other instruments can also be used with the described embodiments, for example, instruments that engage the cutouts 59 and/or the bevelled surfaces 590 in addition to or in lieu of the grooves 57a, 57b, and/or the recesses 58a, 58b. Also, receiving parts according to still further embodiments may further include other combinations of instrument engagement surfaces or features, or even other types of instrument engagement surfaces or features not described herein, without departing from the spirit or scope of the invention, so long as receiving parts according to embodiments of the invention are configured to readily engage two or more different types of instrument engagements.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part of a bone anchoring device, the receiving part comprising:

a first end, a second end below the first end, and a central axis extending between the first and second ends;

a rod recess adjacent to the first end for receiving a rod, wherein the rod recess forms two legs;

a groove that extends circumferentially around an outer surface of at least one of the legs, wherein the groove has a downwardly facing upper surface closer to the first end and an upwardly facing lower surface closer to the second end; and a second recess formed on the outer surface of the at least one of the legs that extends radially inwardly closer to the central axis than the groove is to the central axis, wherein the second recess has a downwardly facing upper surface closer to the first end and an upwardly facing lower surface closer to the second end;

wherein at least part of the lower surface of the second recess and at least part of the lower surface of the groove are located at substantially a same axial position on the receiving part, and wherein all of the downwardly facing regions of the upper surface of the second recess are spaced apart axially from and located closer axially to the first end of the receiving part than the entire upper surface of the groove is to the first end of the receiving part.

2. The receiving part of claim 1, wherein the groove extends circumferentially in an arcuate shape along an entire circumferential extension of the at least one leg.

3. The receiving part of claim 1, wherein a circumferential width of the second recess is less than a circumferential width of the groove.

4. The receiving part of claim 1, wherein the second recess extends circumferentially from a first end to a second end, and wherein a depth of the second recess increases as the second recess extends circumferentially inwardly from the first and second ends towards a middle portion of the second recess.

5. The receiving part of claim 1, wherein at least part of the groove intersects at least part of the second recess.

6. The receiving part of claim 1, wherein at least one of the upper surface or the lower surface of the groove is inclined and extends towards the first end of the receiving part as the at least one surface extends radially inwardly from the outer surface of the receiving part.

7. The receiving part of claim 1, wherein at least one of the upper surface or the lower surface of the second recess extends substantially perpendicularly to the central axis.

8. The receiving part of claim 1, wherein a notch is further formed on the outer surface of the at least one leg, and wherein the notch extends from the upper surface of the second recess towards the first end of the receiving part.

9. The receiving part of claim 1, wherein the at least one leg comprises a cutout at a circumferential end of the leg that is adjacent to the rod recess, and wherein the cutout extends axially from a first end that is located at a same axial position as the upper surface of the groove to a second end that is positioned lower axially than the lower surface of the groove.

10. The receiving part of claim 1, wherein at least one of the groove or the second recess is formed on both of the legs.

11. The receiving part of claim 1, wherein the upper surface of the second recess is distinct from the upper surface of the groove and extends circumferentially while maintaining a substantially constant axial position relative to the receiving part.

12. A coupling device for coupling a bone anchoring element to a rod, the bone anchoring element comprising a shank for anchoring to bone and a head, wherein the coupling device comprises:

the receiving part of claim 1, wherein the receiving part further defines an accommodation space for accommodating the head of the bone anchoring element; and a locking device configured to cooperate with the receiving part to lock the head relative to the receiving part.

13. A receiving part of a bone anchoring device, the receiving part comprising:

a first end, a second end below the first end, and a central axis extending between the first and second ends;

a rod recess adjacent to the first end for receiving a rod, wherein the rod recess forms two legs;

a groove that extends circumferentially around an outer surface of at least one of the legs, wherein the groove has a downwardly facing upper surface closer to the first end and an upwardly facing lower surface closer to the second end; and a second recess formed on the outer surface of the at least one of the legs, wherein the second recess has a downwardly facing upper surface closer to the first end and an upwardly facing lower surface closer to the second end, wherein a circumferential width of the second recess is less than a circumferential width of the groove, and wherein the upper surface of the second recess is distinct from the upper surface of the groove and extends circumferentially while maintaining a substantially constant axial position relative to the receiving part.

14. The receiving part of claim 13, wherein the second recess extends radially inwardly closer to the central axis than the groove is to the central axis.

15. The receiving part of claim 13, wherein the upper surface of the second recess is closer axially to the first end of the receiving part than the upper surface of the groove is to the first end of the receiving part.

16. The receiving part of claim 13, wherein the groove extends circumferentially in an arcuate shape along an entire circumferential extension of the at least one leg.

17. The receiving part of claim 13, wherein at least part of the groove intersects at least part of the second recess.

18. A system comprising:

a receiving part of a bone anchoring device, the receiving part comprising:

a first end, a second end below the first end, and a central axis extending between the first and second ends;

a rod recess adjacent to the first end for receiving a rod, wherein the rod recess forms two legs;

a groove that extends circumferentially around an outer surface of at least one of the legs, wherein the groove has a downwardly facing upper surface closer to the first end and an upwardly facing lower surface closer to the second end, wherein at least one of the upper or lower surfaces of the groove extends circumferentially while maintaining a substantially constant axial position relative to the receiving part; and a second recess formed on the outer surface of the at least one of the legs, wherein the second recess has a downwardly facing upper surface closer to the first end and an upwardly facing lower surface closer to the second end, wherein at least part of the second recess intersects at least part of the groove, wherein at least one of the upper or lower surfaces of the second recess extends circumferentially while maintaining a substantially constant axial position relative to the receiving part;

a first instrument comprising a circumferentially extending rib configured to engage the groove of the receiving part; and a second instrument comprising a protrusion configured to engage the second recess of the receiving part.

19. The system of claim 18, wherein at least one of the first instrument or the second instrument comprises a tubular portion with two arms, and wherein the circumferentially extending rib or the protrusion is formed on an inner surface of at least one of the arms.

\* \* \* \* \*